United States Patent
Yano et al.

(10) Patent No.: US 11,988,657 B2
(45) Date of Patent: May 21, 2024

(54) METHOD FOR DETERMINING DEGREE OF SLUDGE GENERATION IN OIL

(71) Applicant: MITSUBISHI HEAVY INDUSTRIES, LTD., Tokyo (JP)

(72) Inventors: Akihiko Yano, Tokyo (JP); Akihiro Nozaki, Tokyo (JP)

(73) Assignee: MITSUBISHI HEAVY INDUSTRIES, LTD., Tokyo (JP)

( * ) Notice: Subject to any disclaimer, the term of this patent is extended or adjusted under 35 U.S.C. 154(b) by 534 days.

(21) Appl. No.: 17/271,011

(22) PCT Filed: Sep. 19, 2019

(86) PCT No.: PCT/JP2019/036688
§ 371 (c)(1),
(2) Date: Feb. 24, 2021

(87) PCT Pub. No.: WO2020/059776
PCT Pub. Date: Mar. 26, 2020

(65) Prior Publication Data
US 2021/0325363 A1    Oct. 21, 2021

(30) Foreign Application Priority Data

Sep. 19, 2018 (JP) .................................. 2018-175297

(51) Int. Cl.
*G01N 33/28* (2006.01)
*G01N 33/30* (2006.01)

(52) U.S. Cl.
CPC ......... *G01N 33/2888* (2013.01); *G01N 33/30* (2013.01)

(58) Field of Classification Search
CPC .......................... G01N 33/2888; G01N 33/30
See application file for complete search history.

(56) References Cited

FOREIGN PATENT DOCUMENTS

| EP | 0 978 554 | 2/2000 |
|----|-----------|--------|
| JP | 7-34078   | 2/1995 |

(Continued)

OTHER PUBLICATIONS

"Study on the evaluation method of sludge formation during the oxidation process of gear oils" by Yano et al. (Year: 2013).*

(Continued)

*Primary Examiner* — Xin Y Zhong
(74) *Attorney, Agent, or Firm* — Wenderoth, Lind & Ponack, L.L.P.

(57) ABSTRACT

A method for determining the degree of sludge generation in oil includes: a deteriorated oil generating step ST1; a RPVOT testing step ST2; a sludge amount measuring step ST2B; and a determining step ST3. The step ST1 generates deteriorated oil oxidized by immersing and rotating a pressurized container in a thermostatic bath having a predetermined temperature. The pressurized container is pressurized until the oxygen partial pressure reaches a predetermined pressure higher than the value under atmospheric pressure by adding oil and a copper catalyst, substituting with oxygen, or injecting oxygen or air. The step ST2A measures an RPVOT residual ratio of a portion of generated deteriorated oil by the RPVOT test. The step ST2B measures the amount of sludge for a portion of generated deteriorated oil. The step ST3 determines the ease of sludge generation from the relationship between the measured RPVOT residual ratio and the amount of sludge.

4 Claims, 4 Drawing Sheets

(56) References Cited

FOREIGN PATENT DOCUMENTS

| JP | 9-272887   | 10/1997 |
|----|------------|---------|
| JP | 2000-63879 | 2/2000  |
| JP | 2003035706 | 2/2003  |
| JP | 4209093    | 1/2009  |
| JP | 2015-59866 | 3/2015  |
| JP | 2016042029 | 3/2016  |

OTHER PUBLICATIONS

"Standard Test Method for Oxidation Stability of Steam Turbine Oils by Rotating Pressure Vessel", D2272-98 (Year: 1998).*

International Search Report issued Nov. 19, 2019 in International (PCT) Patent Application No. PCT/JP2019/036688.

Written Opinion of the International Searching Authority issued Nov. 19, 2019 in International (PCT) Patent Application No. PCT/JP2019/036688.

Extended European Search Report issued Jul. 27, 2021 in corresponding European Patent Application No. 19863280.4.

"Dry Toast Deposit Control Test Method", Exxon Mobil Corporation, 2016, 4 pages.

Communication pursuant to Article 94(3) EPC dated Feb. 9, 2024 in European Patent Application No. 19863280.4.

Astm: "ASTM D2272-14, Test Method for Oxidation Stability of Steam Turbine Oils by Rotating Pressure Vessel", Aug. 1, 2014.

* cited by examiner

FIG. 3

| ITEM | Dry TOST TEST | DEGRADED OIL GENERATING STEP | RPVOT TEST (ASTM D2272) |
|---|---|---|---|
| AMOUNT OF OIL | 360 ml | 60 g | 50 g |
| TEMPERATURE | 120 °C | Tref = 150 °C | 150 °C |
| OXYGEN | ATMOSPHERIC PRESSURE (3 L / min) | Pref = 0.62 MPa | 0.62 MPa |
| WATER | NONE | NONE | 5 ml |
| CATALYST | IRON AND COPPER (EACH OF WHICH HAS DIAMETER ($\phi$) OF 1.6 mm AND LENGTH OF 3 m) | COPPER (HAVING DIAMETER ($\phi$) OF 1.6 mm AND LENGTH OF 3 m) | COPPER (HAVING DIAMETER ($\phi$) OF 1.6 mm AND LENGTH OF 3 m) |

METHOD FOR DETERMINING DEGREE OF SLUDGE GENERATION IN OIL

TECHNICAL FIELD

The present invention relates to a method for determining the degree of sludge generation in oil.

BACKGROUND ART

In the related art, techniques for determining the performance of oil, which is used for various purposes, have been known in order to increase the service life of the oil. For example, since a lubricant used to lubricate bearings of a turbine is used in large quantities and is used while being partially changed in some units on a regular basis, the long service life of the lubricant is required. The ease of generation of sludge associated with degradation caused by oxidation is used as one of indexes representing the long life of oil. In a case where sludge is generated during degradation, sludge is deposited on, for example, a bearing surface or a rise in the temperature of a bearing is caused. As a result, there is a possibility that the trip or check of the turbine may be required. For this reason, it is important to grasp the tendency of the amount of sludge generated during the degradation of oil.

Japanese Patent No. 4209093 discloses a determination method for determining the ease of generation of sludge in a lubricant according to an RBOT residual ratio by generating degraded oil using an oxidation degradation test for a lubricant, obtaining the RBOT residual ratio, which is a degradation index, of the generated degraded oil by an RBOT test (a rotating bombe oxidation test, an RPVOT test), and obtaining the weight of sludge (filtration residue).

SUMMARY OF INVENTION

Technical Problem

In the determination method disclosed in Japanese Patent No. 4209093, a TOST test (turbine oil stability test) is applied as the oxidation degradation test for generating degraded oil to generate degraded oil. The TOST test is a test for oxidizing a lubricant by putting water, the lubricant, and a copper catalyst and an iron catalyst in a test tube and blowing oxygen under the atmospheric pressure while immersing the test tube in a thermostatic bath having a temperature of 95° C. A Dry TOST test for accelerating the oxidation of a lubricant by setting the temperature of a thermostatic bath to 120° C. without adding water is used in the oxidation degradation test disclosed in Japanese Patent No. 4209093. However, even in the Dry TOST test, a time of about 500 hours to about 3000 hours is required to sufficiently degrade a lubricant. For this reason, there is a problem that a test for determining the ease of generation of sludge cannot be quickly executed.

The present invention has been made in consideration of the above, and an object of the present invention is to more quickly determine the ease of generation of sludge caused by the degradation of oil.

Solution to Problem

In order to solve the above-mentioned problem and to achieve the object, a method for determining a degree of sludge generation in oil according to an aspect of the present invention includes: a step of generating degraded oil, which is obtained from oxidation of oil, by immersing and rotating a pressurized vessel, in which oil and a copper catalyst are put and which is pressurized by substitution of gas with oxygen or injection of oxygen or air until oxygen partial pressure reaches a predetermined pressure higher than a value thereof under an atmospheric pressure, in a thermostatic bath having a predetermined temperature; a step of measuring an RPVOT residual ratio, which is an index value representing a degree of degradation of the degraded oil caused by oxidation, of a part of the generated degraded oil by an RPVOT test and measuring a weight of sludge, which is filtration residue, thereof; and a step of determining ease of generation of the sludge caused by the degradation of the oil from a relationship between the measured RPVOT residual ratio and the measured weight of the sludge.

According to this configuration, in the step of generating the degraded oil, oil is oxidized through the substitution of gas with oxygen or the injection of oxygen or air in a state where oxygen partial pressure is lower than the predetermined pressure higher than the value thereof under the atmospheric pressure. Accordingly, degraded oil can be obtained quickly. Further, the RPVOT residual ratio of a part of the generated degraded oil is measured in an RPVOT testing step, and the amount of sludge, which is filtration residue, thereof is measured. Accordingly, the RPVOT residual ratio and the amount of sludge of the degraded oil can be measured in parallel. As a result, in a case where the obtained RPVOT residual ratio and the obtained amount of sludge are caused to be associated with each other, the ease of generation of sludge caused by the degradation of the oil can be more quickly determined.

Further, it is preferable that the predetermined pressure is in a range of 0.3 (MPa) to 1.0 (MPa).

According to this configuration, the degraded oil can be obtained quickly in the step of generating the degraded oil.

Furthermore, it is preferable that the predetermined temperature is in a range of 130 (° C.) to 150 (° C.).

According to this configuration, the degraded oil can be obtained quickly in the step of generating the degraded oil.

Moreover, it is preferable that a first period in which an estimated value of the RPVOT residual ratio is substantially 0(%) since pressure in the pressurized vessel is reduced to the predetermined pressure from a maximum pressure is specified, the step of generating the degraded oil is executed for a second period shorter than the first period, and the second period is adjusted according to a value of the RPVOT residual ratio of the degraded oil to be generated.

According to this configuration, it is possible to accurately generate degraded oil close to a desired RPVOT residual ratio in the step of generating the degraded oil only by adjusting the second period.

It is preferable that the degraded oil is generated in the step of generating the degraded oil using a test device used in the RPVOT test.

According to this configuration, since both the step of generating the degraded oil and the step of executing the RPVOT test can be executed as long as there is only the test device used in the RPVOT test, a plurality of types of test devices do not need to be prepared. Accordingly, costs can be reduced.

Further, it is preferable that the RPVOT test is a test defined in ASTM D2272.

BRIEF DESCRIPTION OF DRAWINGS

FIG. 3 is a diagram illustrating the respective test conditions of the method for determining the degree of sludge generation in oil according to the embodiment.

DESCRIPTION OF EMBODIMENTS

A method for determining the degree of sludge generation in oil according to an embodiment of the present invention will be described in detail below with reference to the drawings. The present invention is not limited by the present embodiment.

Figure 1:
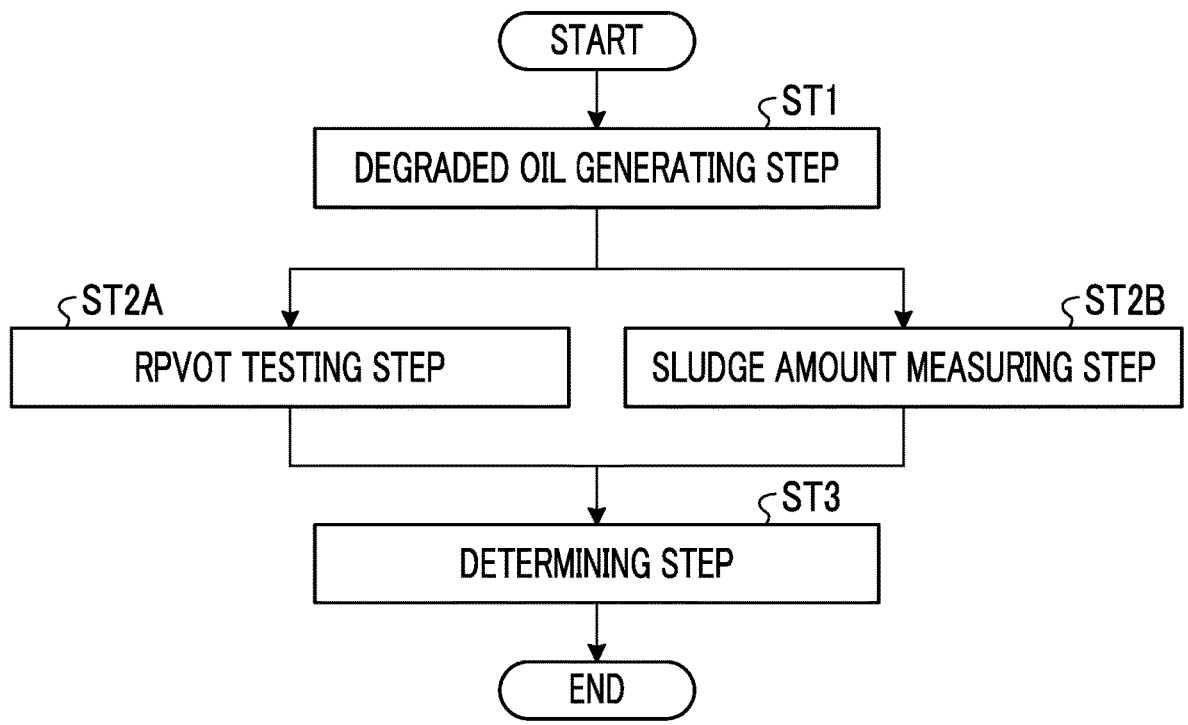
FIG. 1 is a flowchart showing an example of a method for determining the degree of sludge generation in oil according to an embodiment.

FIG. 1 is a flowchart showing an example of a method for determining the degree of sludge generation in oil according to the embodiment. The method for determining the degree of sludge generation in oil according to the embodiment is, for example, a method that is used to grasp the tendency of the weight of sludge (the weight of filtration residue) generated during degradation in a lubricant for lubricating bearings and the like of a turbine and to determine the degree of sludge generation in the lubricant according to the degree of degradation. The method for determining the degree of sludge generation in oil according to the embodiment may be executed about oil other than the lubricant for lubricating bearings and the like of a turbine.

As shown in FIG. 1, the method for determining the degree of sludge generation in oil according to the embodiment includes a degraded oil generating step ST1, a Rotating Pressure Vessel Oxidation Test (RPVOT) testing step ST2A, a sludge amount measuring step ST2B, and a determining step ST3. Each treatment shown in FIG. 1 is executed by a worker using various devices.

First, a worker executes the degraded oil generating step ST1. The degraded oil generating step ST1 is a step of generating degraded oil, which is obtained from the oxidation of oil, by immersing and rotating a pressurized vessel, in which oil and a copper catalyst are put and which is pressurized by the substitution of gas with oxygen or the injection of oxygen or air until oxygen partial pressure reaches a predetermined pressure Pref (see FIG. 3) higher than the value thereof under the atmospheric pressure, in a thermostatic bath having a predetermined temperature. The degraded oil generating step ST1 is executed by a worker using a test device used in a rotating pressure vessel oxidation test (hereinafter, referred to as an "RPVOT test") that is a type of an oxidation degradation test for oil.

Figure 2:
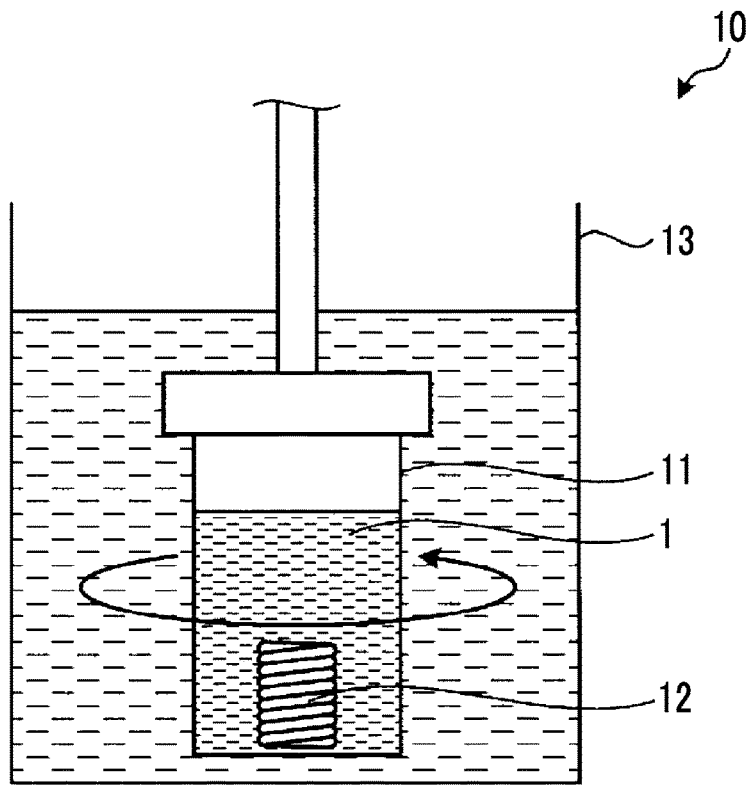
FIG. 2 is a schematic diagram showing an RPVOT test device used in an RPVOT test.

FIG. 2 is a schematic diagram showing an RPVOT test device used in the RPVOT test. As shown in FIG. 2, the RPVOT test device 10 includes a pressurized vessel 11, a copper catalyst 12, and a thermostatic bath 13. The pressurized vessel 11 is a bombe (pressure-resistant vessel) which can be pressurized by the substitution of gas with oxygen or the injection of oxygen or air so that oxygen partial pressure reaches the predetermined pressure Pref. In the degraded oil generating step ST1, a lubricant 1 as a sample and the copper catalyst 12 for promoting the oxidation of the lubricant 1 are disposed in the pressurized vessel 11. The pressurized vessel 11 is adapted to be capable of being rotated in the thermostatic bath 13 by power supplied from a driving source (for example, a motor) (not shown). Further, pressure in the pressurized vessel 11 is detected by pressure measurement equipment (not shown). The copper catalyst 12 is a copper catalyst and is formed in a coil shape in the present embodiment. The thermostatic bath 13 is maintained at a predetermined temperature and the pressurized vessel 11 is immersed in the thermostatic bath 13.

In the degraded oil generating step ST1, the lubricant 1 and the copper catalyst 12 are put in the pressurized vessel 11. Next, oxygen is injected into the pressurized vessel 11 so that the oxygen partial pressure in the pressurized vessel 11 is set to the predetermined pressure Pref higher than the value thereof under the atmospheric pressure, and the pressurized vessel 11 is immersed in the thermostatic bath 13 having a predetermined temperature Tref (see FIG. 3) and is rotated in the thermostatic bath 13 by power supplied from the driving source (not shown). The degraded oil generating step ST1 is executed for an execution time t (see FIG. 4) from a timing when the thermostatic bath 13 is immersed in the pressurized vessel 11 as a starting point of time. Accordingly, degraded oil obtained from the oxidation of the lubricant 1 present in the pressurized vessel 11 is generated.

In the present embodiment, the degraded oil generating step ST1 is executed about the same type of lubricant 1 multiple times with a change in an execution time t to generate a plurality of degraded oils having different RPVOT residual ratios to be described later. Here, an RPVOT residual ratio is an index value representing the degree of degradation of degraded oil caused by oxidation, and the actual measured value of an RPVOT residual ratio is measured in an RPVOT testing step ST2A that is a subsequent step. An RPVOT residual ratio is 100% in new oil, and has a smaller value as the degradation of degraded oil caused by oxidation progresses. In the present embodiment, two sets of degraded oils having the same RPVOT residual ratio are generated in a case where two sets of degraded oil generating steps ST1 are executed for the same execution time t.

The execution conditions of the degraded oil generating step ST1 will be described with reference to FIG. 3. FIG. 3 is a diagram illustrating the respective test conditions of the method for determining the degree of sludge generation in oil according to the embodiment. A middle column in FIG. 3 shows the test conditions of the degraded oil generating step ST1. Further, for comparison, the test conditions of a Dry TOST test defined in ASTM D7873 are added to the left column in FIG. 3. The Dry TOST test is a test method for oxidizing a lubricant by putting 360 ml of the lubricant and a copper catalyst and an iron catalyst (each of which is a coil having a diameter ($\phi$)) of 1.6 mm and a length of 3 m) in a test tube without the addition of water and blowing oxygen under the atmospheric pressure at a rate of 3 L/min while immersing the test tube in a thermostatic bath having a temperature of 120° C. There is a case where an execution time of about 500 hours to about 3000 hours is required to generate degraded oil of which the RPVOT residual ratio is sufficiently reduced depending on the type of the lubricant 1 in this Dry TOST test.

In the degraded oil generating step ST1 according to the embodiment, the amount of the lubricant 1 for each set is set to 60 (g) as shown in FIG. 3. Since two sets of degraded oil generating steps ST1 are executed in the present embodiment, degraded oil is separately generated two times using a total of 120 (g) of the lubricant 1 as a sample. Accordingly, a sufficient amount of degraded oil to be used in the RPVOT testing step ST2A and the sludge amount measuring step ST2B to be described later can be generated.

In the degraded oil generating step ST1, the predetermined temperature Tref of the thermostatic bath 13 is set to 150° C. Since the predetermined temperature of the thermostatic bath 13 is set to 150° C. higher than 120° C. of the Dry TOST test as described above, the oxidation of the lubricant 1 can be accelerated. The predetermined temperature Tref of the thermostatic bath 13 may be in the range of 130° C. to 150° C. In a case where the predetermined temperature Tref is set to 130° C. or more, a temperature can be increased from 120° C. of the Dry TOST test by 10° C. Accordingly, it is said that the oxidation of the lubricant 1 can be suitably accelerated. Further, in a case where the predetermined temperature Tref is set to 150° C. or less, thermal decomposition occurs in the lubricant. Accordingly, it is possible to reduce a concern that the lubricant may be degraded in a mode different from the assumed degradation caused by oxidation.

In the degraded oil generating step ST1, the predetermined pressure Pref of the oxygen partial pressure of the pressurized vessel 11 caused by the injection of oxygen is set to 0.62 MPa higher than the value thereof under the atmospheric pressure. Since the oxygen partial pressure of the pressurized vessel 11 is increased to be higher than the value thereof under the atmospheric pressure that is the test condition of the Dry TOST test in this way, the oxidation of the lubricant 1 can be accelerated. The predetermined pressure Pref may be a value in the range of 0.3 (MPa) to 1.0 (MPa). Not oxygen but air may be injected to set the oxygen partial pressure of the pressurized vessel 11 to the predetermined pressure Pref. Further, gas in the pressurized vessel 11 may be substituted with oxygen, that is, oxygen atmosphere may be formed in the entire pressurized vessel 11.

A coiled copper wire having a diameter ($\phi$)) of 1.6 mm and a length of 3 m is used as the copper catalyst 12.

Figure 4:
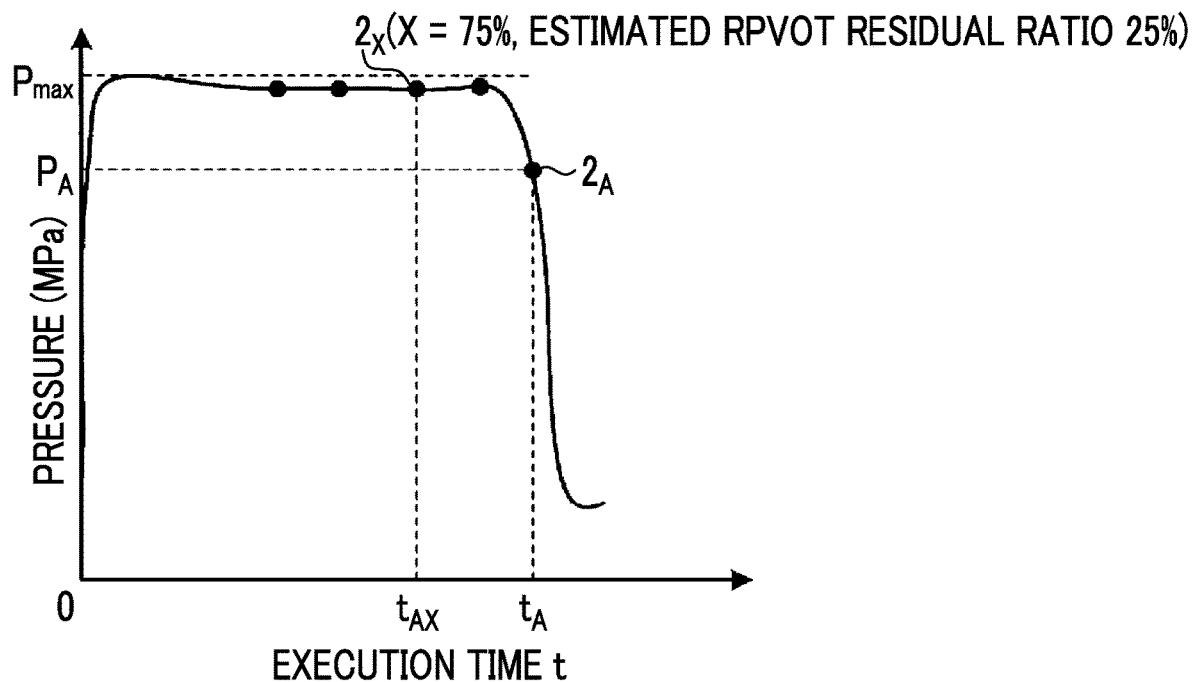
FIG. 4 is a diagram illustrating an example of a change in pressure in a pressurized vessel over the execution time of a degraded oil generating step.

Next, execution times t required to generate degraded oil having different RPVOT residual ratios in the degraded oil generating step ST1 will be described with reference to FIG. 4. FIG. 4 is a diagram illustrating an example of a change in pressure in the pressurized vessel over the execution time of the degraded oil generating step. As shown in FIG. 4, pressure in the pressurized vessel 11 becomes the maximum pressure $P_{max}$ after the start of the degraded oil generating step ST1 (after the pressurized vessel 11 is immersed in the thermostatic bath 13), and pressure starts to be reduced at a certain point of time in a case where the degraded oil generating step ST1 is further continued. That is, since oxygen present in the pressurized vessel 11 is consumed for the oxidation of the lubricant 1, pressure in the pressurized vessel 11 is reduced. Here, time, which has passed from the starting point of time until pressure in the pressurized vessel 11 reaches a predetermined pressure $P_A$ from the maximum pressure $P_{max}$, is referred to as an RPVOT value to of the degraded oil generating step ST1. In the present embodiment, the predetermined pressure $P_A$ has a value that is obtained in a case where a pressure of 0.175 MPa is reduced from the maximum pressure $P_{max}$. The predetermined pressure $P_A$ may have, for example, a value that is obtained in a case where a pressure in the range of 0.170 MPa to 0.180 MPa is reduced from the maximum pressure $P_{max}$. The RPVOT value $t_A$ can be measured in a case where the degraded oil generating step ST1 is executed under the test conditions of the degraded oil generating step ST1 shown in FIG. 3 until pressure in the pressurized vessel 11 reaches the pressure $P_A$ obtained in a case where a pressure of 0.175 MPa is reduced from the maximum pressure $P_{max}$.

It is assumed that the degraded oil generating step ST1 is executed for an execution time $t_{AX}$ corresponding to a ratio of X % of the measured RPVOT value $t_A$. In this case, it can be estimated that only X % of degraded oil $2_A$, which is generated in a case where the degraded oil generating step ST1 is continued until the RPVOT value $t_A$, is degraded in generated degraded oil $2_X$ due to oxidation. As described above, an RPVOT residual ratio, which is the index of the degree of degradation of degraded oil, is 100% in new oil, and has a smaller value as the oxidation of degraded oil progresses. Since it is thought that the oxidation of the degraded oil $2_A$, which is generated in a case where the degraded oil generating step ST1 is continued until the RPVOT value $t_A$, has completely progressed, it can be estimated that the RPVOT residual ratio of the degraded oil is substantially 0% (for example, the range of 0% to 3%). That is, the RPVOT value $t_A$ mentioned here is a first period in which the estimated value of an RPVOT residual ratio is substantially 0% since pressure in the pressurized vessel 11 is reduced to the predetermined pressure $P_A$ from the maximum pressure $P_{max}$. Accordingly, it can be estimated that the degraded oil $2_X$ in which only X % of the degraded oil $2_A$ is degraded due to oxidation has an RPVOT residual ratio of (100-X) %. The estimated value of the RPVOT residual ratio of the degraded oil $2_X$ is referred to as an estimated RPVOT residual ratio (%). For example, in FIG. 4, degraded oil $2_X$ (X=75%), which is generated in a case where the degraded oil generating step ST1 is executed for the time of X % (=75%) of the RPVOT value $t_A$, has an estimated RPVOT residual ratio of 25%. As described above, the degraded oil $2_X$ having a desired estimated RPVOT residual ratio can be generated in a case where the degraded oil generating step ST1 is executed for an execution time $t_{AX}$ corresponding to X % of the RPVOT value $t_A$, that is, a second period shorter than the first period. In other words, the execution time $t_{AX}$, which is the second period, is adjusted according to the value of the RPVOT residual ratio of the degraded oil $2_X$ to be generated.

Figure 5:
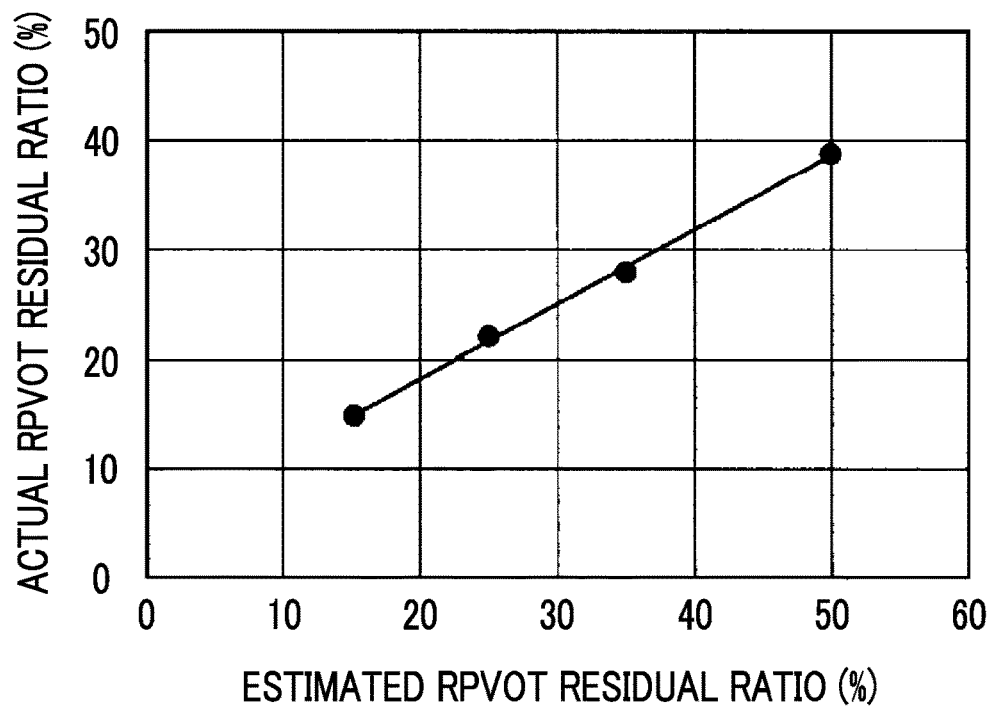
FIG. 5 is a diagram illustrating an example of a relationship between an estimated RPVOT residual ratio and an actual RPVOT residual ratio.

FIG. 5 is a diagram illustrating an example of a relationship between an estimated RPVOT residual ratio and an actual RPVOT residual ratio. The actual RPVOT residual ratio is a value that is measured about each degraded oil $2_X$ generated in the degraded oil generating step ST1 by an RPVOT test defined in ASTM D2272 to be described later. As shown in FIG. 5, the estimated RPVOT residual ratio and the actual RPVOT residual ratio are not completely equal to each other but are values close to each other. For this reason, it is possible to obtain the degraded oil $2_X$ relatively close to degraded oil having an RPVOT residual ratio about which a worker wants to acquire data in the RPVOT testing step ST2A and the sludge amount measuring step ST2B that are subsequent steps.

Further, the estimated RPVOT residual ratio and the actual RPVOT residual ratio are in a linear relationship as shown in FIG. 5. Accordingly, in a case where at least two points among points shown in FIG. 5 are acquired, it is possible to more accurately generate degraded oil, which is close to an RPVOT residual ratio about which a worker wants to acquire data in the subsequent steps, by adjusting the estimated RPVOT residual ratio on the basis of the linear relationship. As a result, for example, only a part of degraded oil is generated in the degraded oil generating step ST1, and it is also possible to more accurately generate remaining degraded oil by executing the degraded oil generating step ST1 again while adjusting the estimated RPVOT residual ratio on the basis of the linear relationship after acquiring two points among the points shown in FIG. 5 by executing the RPVOT testing step ST2A to be described later on the generated degraded oil.

Next, a worker executes the RPVOT testing step ST2A and the sludge amount measuring step ST2B. The RPVOT testing step ST2A and the sludge amount measuring step ST2B may be executed in parallel, or may be sequentially executed from any one of them. Further, the RPVOT testing step ST2A and the sludge amount measuring step ST2B are not steps that cannot be executed until all the degraded oils are generated in the degraded oil generating step ST1. The RPVOT testing step ST2A and the sludge amount measuring step ST2B may be executed at a timing when at least one type of degraded oil is generated.

The RPVOT testing step ST2A is a step of measuring an RPVOT residual ratio of a part of the generated degraded oil by the RPVOT test defined in ASTM D2272. The RPVOT testing step ST2A is executed using one set of the two sets of degraded oils that are generated in the degraded oil generating step ST1 and have the same RPVOT residual ratio. The RPVOT testing step ST2A is executed using the RPVOT test device 10 shown in FIG. 2. However, the degraded oil generating step ST1 and the RPVOT testing step ST2A do not need to be executed using a single RPVOT test device 10.

The RPVOT testing step ST2A is executed according to the test conditions of the RPVOT test defined in ASTM D2272 shown in the right column in FIG. 3. In more detail, in the RPVOT testing step ST2A, 50 g of one set of degraded oil generated in the degraded oil generating step ST1, 5 ml of water, and a coiled copper catalyst 12 having a diameter ($\phi$)) of 1.6 mm and a length of 3 m are put in the pressurized vessel 11. Next, gas in the pressurized vessel 11 is substituted with oxygen to form oxygen atmosphere in the pressurized vessel 11, pressure (that is, oxygen pressure) in the pressurized vessel 11 is set to 0.62 MPa higher than the value thereof under the atmospheric pressure, and the pressurized vessel 11 is immersed in the thermostatic bath 13 having a temperature of 150° C. and is rotated in the thermostatic bath 13 by power supplied from the driving source (not shown). Then, a RPVOT value, which is the time having passed from a point of time when the pressurized vessel 11 is immersed in the thermostatic bath 13 until pressure in the pressurized vessel 11 is reduced to 0.175 MPa from the maximum pressure, is measured. That is, since oxygen present in the pressurized vessel 11 is consumed for the further oxidation of the degraded oil, pressure in the pressurized vessel 11 is reduced. Accordingly, since time required for the RPVOT test is shortened as the original degraded oil is oxidized, a RPVOT value is reduced.

In the RPVOT testing step ST2A, the RPVOT test is executed about all types of degraded oils, which are generated in the degraded oil generating step ST1 and have different RPVOT residual ratios, according to the above-mentioned test conditions shown in FIG. 3 to measure the RPVOT values of all types of degraded oils. Further, in the RPVOT testing step ST2A, the RPVOT test is executed about even new oil of the lubricant 1 according to the test conditions shown in FIG. 3 as in the case of the degraded oil to measure the RPVOT value of the new oil. Accordingly, the measured RPVOT value of each degraded oil is divided by the RPVOT value of the new oil to calculate the actual RPVOT residual ratio (%) of each degraded oil. That is, an RPVOT residual ratio is a ratio of the RPVOT value of the degraded oil to the RPVOT value of the new oil. As described above, an RPVOT residual ratio is 100% in the new oil and has a smaller value as the degradation of the degraded oil caused by oxidation progresses. The RPVOT testing step ST2A may be executed with a standard other than ASTM D2272 as long as the actual RPVOT residual ratio (%) of the degraded oil can be measured.

The sludge amount measuring step ST2B is a step of measuring the weight of sludge, which is filtration residue, of a remaining part of the generated degraded oil. The sludge amount measuring step ST2B is executed using remaining one set of degraded oil, which is not used in the RPVOT testing step ST2A, of the two sets of degraded oils that are generated in the degraded oil generating step ST1 and have the same RPVOT residual ratio. In the sludge amount measuring step ST2B, the weight of sludge of each of all types of degraded oils, which are generated in the degraded oil generating step ST1 and have different RPVOT residual ratios, is measured. In more detail, in the sludge amount measuring step ST2B, each degraded oil is filtered by a filtration device (not shown), filtration residue, that is, sludge is acquired, and the weight of the acquired sludge (hereinafter, referred to as the amount of sludge) is measured.

In a case where both the RPVOT testing step ST2A and the sludge amount measuring step ST2B are completed, a worker executes the determining step ST3. The determining step ST3 is a step of associating the measured RPVOT residual ratio with the amount of sludge and determining the ease of generation of sludge caused by the degradation of the lubricant 1. In the present embodiment, the RPVOT residual ratio of each degraded oil measured in the RPVOT testing step ST2A and the amount of sludge of each degraded oil measured in the sludge amount measuring step ST2B are caused to be associated with each other, the amount of sludge is plotted for every RPVOT residual ratio, and the ease of generation of sludge according to the degree of degradation of the lubricant 1 is determined.

Figure 6:
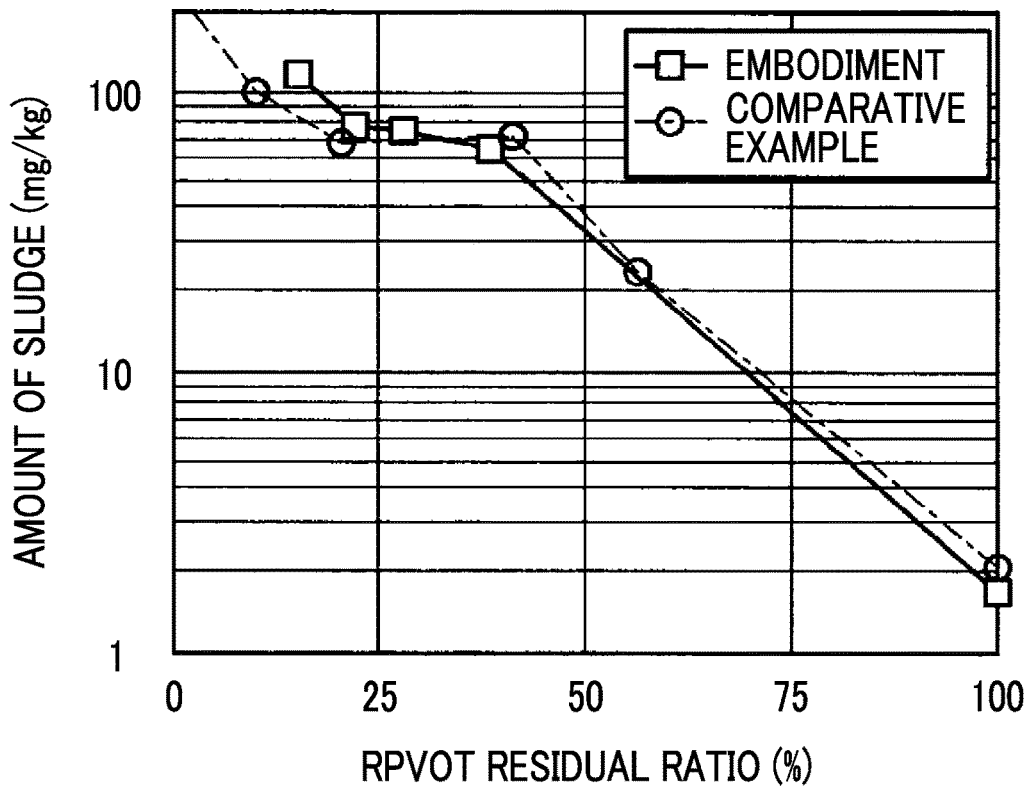
FIG. 6 is a diagram illustrating an example of a relationship between an RPVOT residual ratio measured in an RPVOT testing step and the amount of sludge measured in a sludge amount measuring step.

FIG. 6 is a diagram illustrating an example of a relationship between the RPVOT residual ratio measured in the RPVOT testing step and the amount of sludge measured in the sludge amount measuring step. In FIG. 6, portions other than actual measured points are interpolated by a publicly-known interpolation method. Further, a relationship between a RPVOT residual ratio and the amount of sludge, which is obtained in a case where degraded oil is generated by the Dry TOST test according to the test conditions shown in the left column in FIG. 3 instead of the degraded oil generating step ST1, is also plotted as Comparative example in FIG. 6. The amount of sludge in FIG. 6 is the amount of sludge (mg) per 1 kg of degraded oil.

As shown in FIG. 6, a relationship between the RPVOT residual ratio and the amount of sludge measured in the method for determining the degree of sludge generation in oil according to the present embodiment shows a change tendency substantially close to that of Comparative example. In the example shown in FIG. 6, at an RPVOT residual ratio of 25% as an example of a criterion to be described later, the amount of sludge is 75.8 mg/kg in the method for determining the degree of sludge generation in oil according to the embodiment and the amount of sludge is 68.0 mg/kg in Comparative example. The values of the amount of sludge substantially close to each other are obtained. Further, a deviation between the embodiment and Comparative example is 11.5% in the example shown in FIG. 6. It is said that the ease of generation of sludge according to the degree of degradation of the lubricant 1 can be determined by the method for determining the degree of sludge generation in oil according to the present embodiment with an accuracy close to that of Comparative example corresponding to a case where degraded oil is generated by the Dry TOST test.

Examples of a criterion for determining whether or not the ease of generation of sludge according to the degree of degradation of the lubricant 1 is good includes a condition that the amount of sludge is smaller than a predetermined value in a region where an RPVOT residual ratio is lower than a predetermined RPVOT residual ratio. For example, 25% that is a criterion for a turbine lubricant defined in ASTM D4378 can be employed as the predetermined RPVOT residual ratio. Further, for example, 100 mg/kg can be employed as the predetermined value of the amount of sludge on the basis of results of the occurrence of troubles caused by sludge, such as the clogging of a filter, in an actual turbine.

Figure 7:
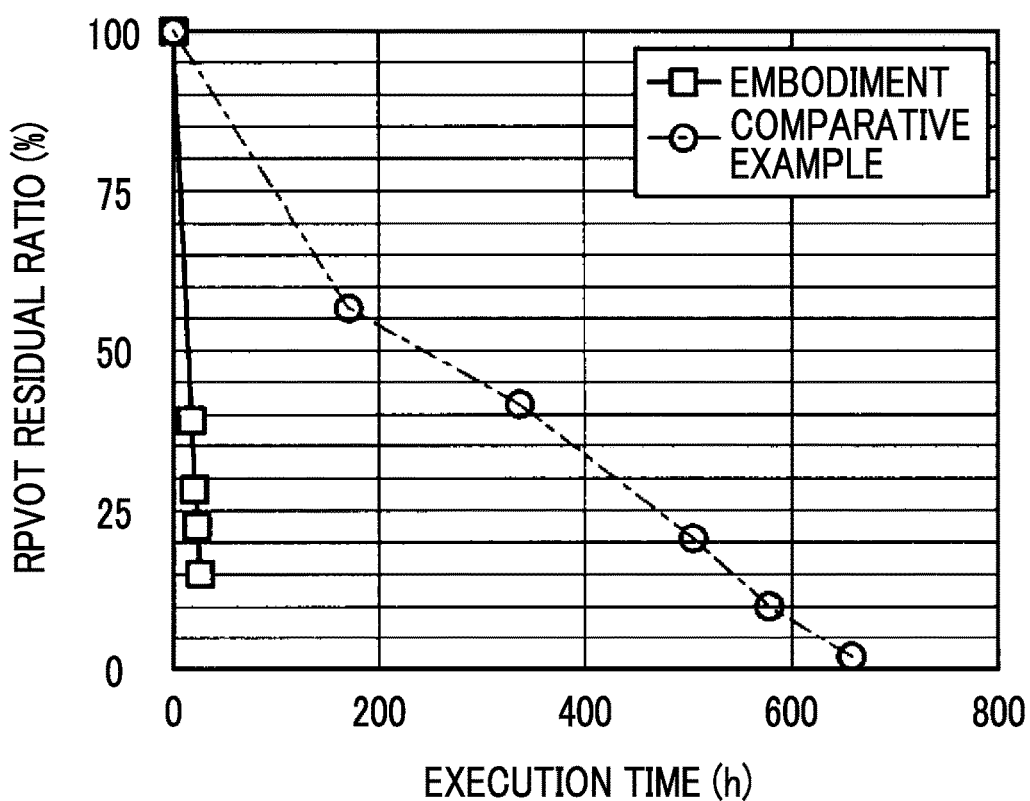
FIG. 7 is a diagram illustrating examples of execution times that are required until degraded oils having different RPVOT residual ratios are generated in the degraded oil generating step.

An effect of accelerating the generation of degraded oil by the method for determining the degree of sludge generation in oil according to the embodiment will be described with reference to FIG. 7. FIG. 7 is a diagram illustrating examples of execution times that are required until degraded oils having different RPVOT residual ratios are generated in the degraded oil generating step. The RPVOT residual ratio mentioned here is an actual RPVOT residual ratio measured in the RPVOT testing step ST2. In FIG. 7, portions other than actual measured points are interpolated by a publicly-known interpolation method. Further, values, which are obtained in a case where degraded oil is generated by the Dry TOST test according to the test conditions shown in the left column in FIG. 3, are also plotted as Comparative example even in FIG. 7 as in FIG. 6. As shown in FIG. 7, 467 hours is required in Comparative example until the RPVOT residual ratio of degraded oil as an example of the above-mentioned criterion reaches 25%. In contrast, only 19.7 hours is required in the method for determining the degree of sludge generation in oil according to the embodiment until the RPVOT residual ratio of degraded oil reaches 25%. Therefore, according to the degraded oil generating step ST1 of the present embodiment, degradation can be accelerated by 23.7 times that of Comparative example.

As described above, in the degraded oil generating step ST1 of the method for determining the degree of sludge generation in oil according to the embodiment, the lubricant 1 is oxidized in a state where oxygen partial pressure is lower than the predetermined pressure Pref higher than the value thereof under the atmospheric pressure, through the substitution of gas with oxygen or the injection of oxygen or air. Accordingly, degraded oil can be obtained quickly. Further, the RPVOT residual ratio of a part (one set) of the generated degraded oils is measured in the RPVOT testing step ST2A, and the amount of sludge of a remaining part (one set) thereof is measured in the sludge amount measuring step ST2B. Accordingly, the RPVOT residual ratio and the amount of sludge of the degraded oil can be measured in parallel. As a result, in a case where the obtained RPVOT residual ratio and the obtained amount of sludge are caused to be associated with each other, the ease of generation of sludge caused by the degradation of the lubricant 1 can be more quickly determined.

Further, it is preferable that the predetermined pressure Pref is in the range of 0.3 (MPa) to 1.0 (MPa). Furthermore, it is more preferable that the predetermined pressure Pref is 0.62 (MPa).

According to this configuration, degraded oil can be obtained quickly in the degraded oil generating step ST1. However, the predetermined pressure Pref may have a value that is higher than the atmospheric pressure and allows the oxidation of the lubricant 1 to be sufficiently accelerated.

Further, it is preferable that the predetermined temperature Tref is in the range of 130 (° C.) to 150 (° C.). Furthermore, it is more preferable that the predetermined temperature Tref is 150 (° C.).

According to this configuration, degraded oil can be obtained quickly in the degraded oil generating step ST1. However, the predetermined temperature Tref may have a value lower than a temperature that allows the oxidation of the lubricant 1 to be accelerated as compared to the Dry TOST test in the related art and allows the lubricant to be degraded in a degradation mode other than oxidation.

Further, the first period (RPVOT value $t_A$) in which the estimated value of an RPVOT residual ratio is substantially 0(%) since pressure in the pressurized vessel 11 is reduced to the predetermined pressure $P_A$ from the maximum pressure $P_{max}$ is specified, the degraded oil generating step ST1 is executed for the second period (execution time $t_{AX}$) shorter than the first period, and the second period is adjusted according to the value of the RPVOT residual ratio of degraded oil to be generated.

According to this configuration, it is possible to accurately generate degraded oil close to a desired RPVOT residual ratio in the degraded oil generating step ST1 only by adjusting the second period (execution time $t_{AX}$). However, a method of determining an execution time t is not limited to the method described in the present embodiment. For example, with regard to a specific type of lubricant 1, a relationship between an execution time t and the actual RPVOT residual ratio of generated degraded oil is accumulated as data by the past execution results and experiments of the method for determining the degree of sludge generation in oil according to the embodiment, and an execution time t may be set on the basis of the accumulated data so that a desired RPVOT residual ratio is obtained. Further, with regard to a specific type of lubricant 1, a pressure $P_A$ and an RPVOT value $t_A$, that are to be obtained in a case where the RPVOT residual ratio is a predetermined residual ratio, for example, substantially 0 (about 3% or less), may be specified in advance on the basis of the accumulated data.

Furthermore, degraded oil is generated in the degraded oil generating step ST1 using the RPVOT test device 10 used in the RPVOT test.

According to this configuration, since both the degraded oil generating step ST1 and the RPVOT testing step ST2A can be executed as long as there is only the RPVOT test device 10 used in the RPVOT test, a plurality of types of test devices do not need to be prepared. Accordingly, costs can be reduced. As described above, a single RPVOT test device 10 does not need to be used in the degraded oil generating step ST1 and the RPVOT testing step ST2A. Further, as long as the contents of treatment described in the present embodiment can be executed, the degraded oil generating step ST1 may be executed using a device different from a dedicated device used in the RPVOT test.

REFERENCE SIGNS LIST

1: lubricant
10: RPVOT test device
11: pressurized vessel
12: copper catalyst
13: thermostatic bath

The invention claimed is:

1. A method for determining a degree of sludge generation in oil, the method comprising:
   a step of generating degraded oil, which is obtained from oxidation of oil, by immersing and rotating a pressurized vessel, in which oil and a copper catalyst are put and which is pressurized by substitution of gas with oxygen or injection of oxygen or air until oxygen partial pressure reaches a maximum pressure higher than a value thereof under an atmospheric pressure, in a thermostatic bath having a predetermined temperature;
   a step of measuring a Rotating Pressure Vessel Oxidation Test (RPVOT) residual ratio, which is an index value representing a degree of degradation of the degraded oil caused by oxidation, of a part of the degraded oil by an RPVOT test and measuring a weight of sludge, which is filtration residue, thereof; and
   a step of determining ease of generation of the sludge caused by the degradation of the oil from a relationship between the measured RPVOT residual ratio and the measured weight of the sludge,
   wherein:
   a first period is specified before the step of generating the degraded oil, pressure in the pressurized vessel being reduced to a predetermined pressure from the maximum pressure such that an estimated value of the RPVOT residual ratio is substantially 0% and excludes 0% in the first period;
   the step of generating the degraded oil is executed for a second period shorter than the first period; and
   the second period is adjusted according to a linear relationship between the estimated value of the RPVOT residual ratio and the measured RPVOT residual ratio.

2. The method according to claim 1, wherein the predetermined pressure is in a range of 0.3 MPa to 1.0 MPa.

3. The method according to claim 1, wherein the predetermined temperature is in a range of 130° C. to 150° C.

4. The method according to claim 1, wherein the degraded oil is generated using a test device used in the RPVOT test.

* * * * *